United States Patent [19]

Goldman

[11] Patent Number: 4,564,011
[45] Date of Patent: Jan. 14, 1986

[54] LASER OPTIC DEVICE AND METHOD

[76] Inventor: Leon Goldman, 2324 Madison Rd., #1807, Cincinnati, Ohio 45208

[21] Appl. No.: 539,160

[22] Filed: Oct. 6, 1983

Related U.S. Application Data

[63] Continuation-in-part of Ser. No. 360,244, Mar. 22, 1982, abandoned.

[51] Int. Cl.⁴ ............................................. A61B 17/36
[52] U.S. Cl. .................................. 128/303.1; 128/398
[58] Field of Search ....................... 128/303.1, 395–398

[56] References Cited

U.S. PATENT DOCUMENTS

| | | | |
|---|---|---|---|
| 3,538,919 | 4/1967 | Meyer | 128/398 |
| 3,703,176 | 11/1972 | Vassiliadis et al. | 128/303.1 |
| 3,720,213 | 3/1973 | Hobart et al. | 128/395 |
| 3,750,670 | 8/1973 | Palanos et al. | 128/303.1 |
| 3,783,874 | 1/1974 | Koester et al. | 128/303.1 |
| 3,821,510 | 6/1974 | Muncheryan | 128/303.1 X |
| 3,858,577 | 1/1975 | Bass et al. | 128/398 X |
| 3,982,541 | 9/1976 | L'Esperance, Jr. | 128/303.1 |
| 4,207,874 | 6/1980 | Choy | 128/303.1 X |
| 4,301,802 | 11/1981 | Poler | 128/303.14 |
| 4,316,467 | 2/1982 | Muckerherde | 128/303.1 |

FOREIGN PATENT DOCUMENTS

| | | | |
|---|---|---|---|
| 2810879 | 10/1978 | Fed. Rep. of Germany | 128/303.1 |
| 2826383 | 12/1979 | Fed. Rep. of Germany | 128/303.1 |

OTHER PUBLICATIONS

Goldman, "Recent Advances . . . Surgery", Med. Surg. Review, pp. 32-35, 1971.

Primary Examiner—Lee S. Cohen
Attorney, Agent, or Firm—Wood, Herron & Evans

[57] ABSTRACT

A laser optic device comprises at least one optic fiber disposed within a protective conduit which is mounted to a disposable probe assembly having a hollow needle insertable within the body. Laser energy is transmitted through the optic fiber to a lens at one end which is adapted to focus the laser energy through the hollow needle and into a blood vessel, for creating a blood clot, or into the tissue immediately adjacent a damaged blood vessel for creating white scar tissue thereby causing the vessel to shrink in size and at least partially disappear from view.

7 Claims, 4 Drawing Figures

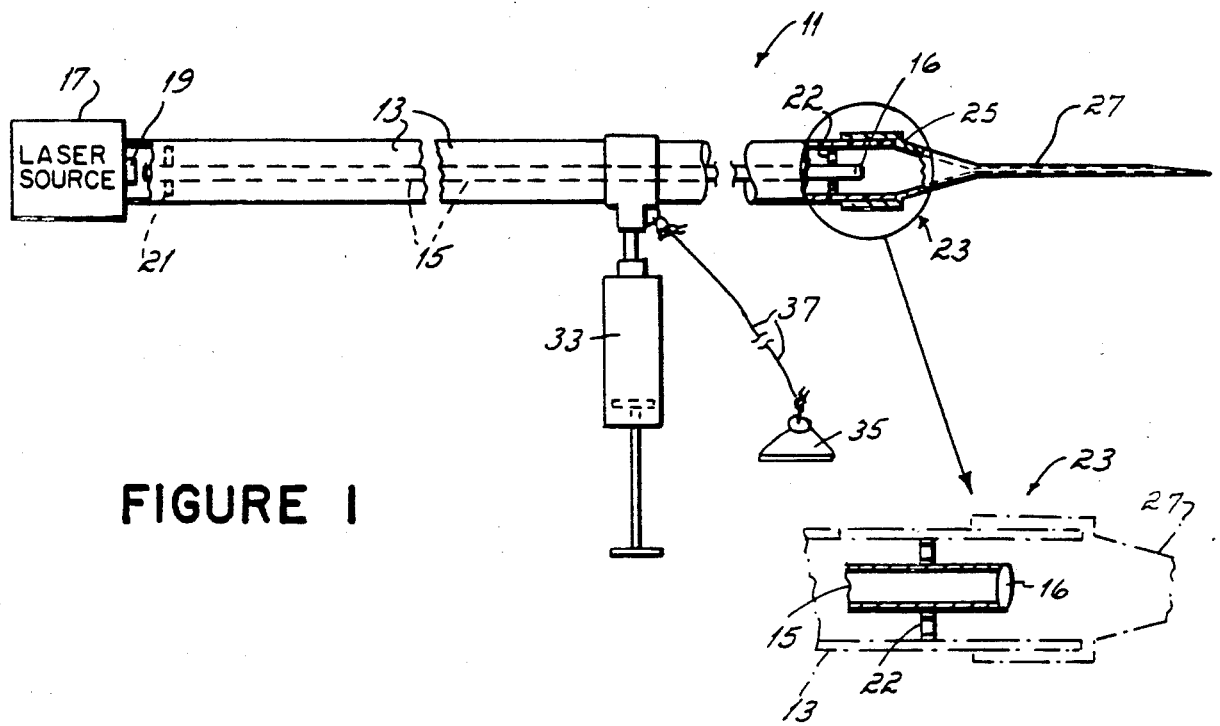
FIGURE 1
FIGURE 1a
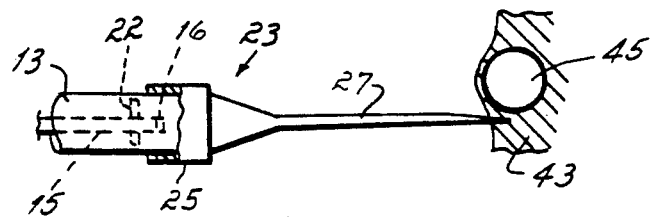
FIGURE 2
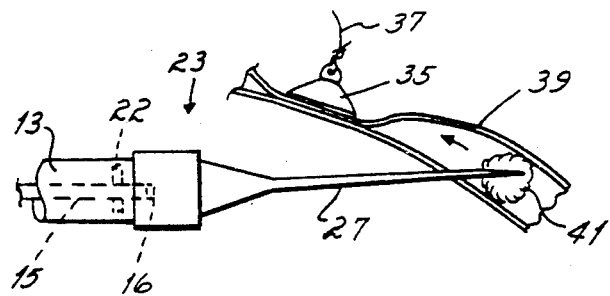
FIGURE 3

LASER OPTIC DEVICE AND METHOD

RELATED APPLICATIONS

This is a continuation-in-part of U.S. application Ser. No. 360,244 filed Mar. 22, 1982 entitled "Laser-Optic Device", now abandoned.

FIELD OF THE INVENTION

This invention relates generally to the field of laser optic instruments, and, more particularly, to an apparatus and method for the treatment of blood vessels and surrounding tissue using laser energy.

BACKGROUND OF THE INVENTION

The use of lasers in medical applications has been increasing at a rapid pace particularly in the last decade. As in well known, lasers produce an intense beam of electromagnetic radiation of high spectral purity or monochromaticity which can be collimated to a fine degree with high radiation densities, small angular divergences and long coherent time. Such properties make lasers particularly attractive for a variety of medical uses.

For example, a process known as photo-coagulation has been developed primarily for medical procedures such as chorioretinal coagulation in which a laser beam is used to achieve fusion of the retina and choroid of the eye to overcome retinal detachments. As discussed for example in U.S. Pat. Nos. 3,720,213 to Hobart, et al; 3,703,176 to Vassiliadas, et al and 3,783,874 to Koester, et al, the process of photo-coagulation as applied to the retina and choroid consists of introducing a laser beam externally upon the cornea of the eye with the energy being directed in such a manner that it is concentrated at a selected point upon the fundus by refractive media of the eye so that tissues in a very localized area are congealed. The above cited patents disclose various devices for directing a laser beam to the appropriate external location on the cornea.

In contrast to laser energy, ultraviolet radiations may injure refractive media of the eye, and radiant energy may be dissipated or conducted into surrounding portions of the eye by the fundus making such forms of treatment unacceptable. The high intensity and small angular divergence of laser beams enables the desired amount of coagulation to occur in a short period of time, to a very confined area, with minimal excessive generation of heat.

In each of the patents discussed above and in virtually all photo-coagulation procedures, particularly chorioretinal coagulation, the laser beam is positioned externally of the eye at a predetermined, carefully defined location. A similar device is disclosed in U.S. Pat. No. 3,750,670 to Balanos, et al in which the repair of a retinal detachment or treatment of blood vessels of diabetics is taught using an apparatus described as a laser cauterizer. This apparatus is similar to the photo-coagulation devices discussed in the patents cited above and also involves external treatment of an affected area by laser energy.

Another medical use for laser energy is disclosed in U.S. Pat. No. 3,538,919 to Meyer. In this patent, a method of depilation by laser energy is taught in which a fiber optics rod covered by a catheter jacket acts as a conduit for delivery of a laser beam to a hollow needle mounted at one end of the fiber optics rod. The needle is inserted alongside a hair follicle and transmits a laser beam to the base of the follicle which is then destroyed by the heat intensity of the beam. Unlike the photo-coagulation use for a laser beam as discussed in the patents above, the Meyer method of depilation involves insertion of a needle or other laser beam transmitting conduit into the body. The high radiation density and small angular divergence property of the laser beam is used to advantage in Meyer wherein only that portion of the follicle in the immediate vicinity of the end of the needle is subjected to the laser energy and destroyed.

Areas of medical treatment in which the capability of laser energy has not been investigated include the intravascular treatment of blood vessels to create clotting, and the cosmetic treatment of unsightly blood vessels. It is therefore one object of this invention to provide an apparatus and method for creating, intravascularly, a blood clot within a vessel of a patient.

It is another object of this invention to provide an apparatus and method for creating scar tissue adjacent and overlapping a disfunctional blood vessel to cosmetically remove it from sight.

SUMMARY OF THE INVENTION

These objectives are accomplished in this invention of a laser optic device for the treatment of blood vessels and tissue including an elongated optic fiber, having a lens at its proximal end, disposed within a flexible catheter. The catheter is connected at its distal end to a source of laser energy, which includes a focusing lens so that the laser beam it produces is directed into the optic fiber and transmitted therealong. The proximal end of the catheter is adapted to mount a disposable probe having a hollow needle. The laser beam transmitted by the optic fiber is focused by its lens into the needle of probe where it exits the instrument. A syringe filled with saline is mounted to the catheter adjacent the probe, and is adapted to inject saline into the probe to clear any obstructions. A pressure ring is also mounted to the catheter for exerting pressure on the blood vessel to be treated.

As discussed in detail below, the apparatus of this invention is primarily intended for the cosmetic treatment of unsightly, damaged blood vessels, although other medical uses are contemplated. In one treatment method, particularly for large blood vessels, the pressure ring is depressed against the vessel and the probe is then inserted directly into the blood vessel downstream from the pressure ring. The source of laser energy is activated to create a heat-induced blood clot at the point where the probe enters the vessel. Flow of blood through the damaged vessel is stopped which eventually forces the blood to flow through alternate routes deeper beneath the surface of the skin. The affected vein shrinks and at least partially disappears from view.

In addition, smaller blood vessels may be treated by placing the probe in the tissue adjacent such vessels. Scar tissue is created by the laser energy emanating from the probe, which tends to squeeze against the vessel to be treated and restricts the blood flow therethrough. The treated vessel shrinks in size as the blood finds alternate paths, and may become partially covered by the white appearance of the adjacent, overlapping scar tissue.

DESCRIPTION OF THE DRAWINGS

The structure, operation and advantages of this invention will become further apparent upon consideration of the following description taken in conjunction with the accompanying drawings, wherein:

FIG. 1 is a side view of the laser optic device according to the invention;

FIG. 1a is an enlarged side view of the proximal end of the device shown in FIG. 1;

FIG. 2 is a view in partial cross-section of a portion of the laser optic device in FIG. 1, shown in cosmetically treating a blood vessel; and FIG. 3 is another view in partial cross-section of the device herein shown in position for creating a clot in a blood vessel.

DETAILED DESCRIPTION OF THE INVENTION

Referring now to the drawings, the laser optic device 11 of this invention includes an elongated catheter 13 in which a commercially available optic fiber 15, having a lens 16 mounted at its proximal end, is concentrically disposed and mounted at each end by a pair of radial holders 21 and 22. The catheter 13 is connected at its distal end to a laser source 17 having a focusing lens 19. The distal end of optic fiber 15 is mounted by radial holder 21 within catheter 13 adjacent the laser source 17 in direct alignment with the focusing lens 19 so as to receive and transmit the laser energy from the laser source 17 to the opposite end of the catheter 13. Although only a single optic fiber 15 is shown in the Figures, it should be understood that several optic fibers could be disposed within catheter 13 for transmitting the laser energy.

A disposable probe 23 is provided including a hub 25 which tapers to form a thin, hollow needle 27. The hub 25 is adapted to snap-fit over the proximal end of the catheter 13 so as to align the needle 27 with the proximal end of optic fiber 15, which is held in position by radial holder 22. The laser energy transmitted by optic fiber 15 from the laser source 17 is focused by the optic fiber lens 16 directly into and through the needle 27 where it exits the laser optic device 11. Therefore, the laser energy from source 17 is precisely directed by the laser optic device 11 to an area approximately the size of the diameter of needle 27.

The laser optic device 11 further includes a syringe 33, containing a rinsing solution such as saline, which is mounted to the catheter 13 and is operable to introduce saline into the catheter 13, past the proximal end of optic fiber 15 and the radial holder 22 into the needle 27 of probe 23. The saline clears blood or other obstructions from the needle 27 as discussed in more detail below. In addition, a pressure pad 35 is attached by a cord 37 to a point along the catheter 13 for purposes to become apparent below.

The advantages of this invention may be best understood by reference to the methods in which the laser optic device 11 may be utilized. In one embodiment, as shown in FIG. 3, the laser optic device 11 is operable to create clotting or coagulation of blood in a vessel. In this procedure, the needle 27 of probe 23 is inserted directly into the blood vessel 39 to be treated. The pressure pad 35 is spaced a short distance from the needle 27 in the direction of the blood flow, and is pressed directly against the vessel 39 to constrict it and prevent the flow of blood therethrough. The laser source 17 is then actuated and laser energy is transmitted through optic fiber 15 and needle 27 directly into the blood vessel 39.

The heat from the laser energy causes a blood clot 41 to develop in the blood vessel 39 adjacent the needle 27. The clot 41 may be enlarged by moving the needle 27 from the initial point of insertion into the blood vessel 39 either toward or away from the pressure pad 35, and then activating the laser source 17 to induce further clotting. During this procedure, the pressure pad 35 is held tightly against the blood vessel 39 at a point spaced from the needle 27 in the direction of the blood flow. The pressure pad 35 performs the dual function of limiting the extent of blocking in the blood vessel 39 and also prevents thromboembolism or the release of fragments of the blood clot 41 into other areas of the body.

The above-described procedure is used primarily for the cosmetic treatment of large blood vessels, although if emergency clotting of the blood is required such as in the case of hemophilia, or in various non-emergency situations, the device 11 would also be advantageous. Elimination or at least partial elimination of a damaged blood vessel from view according to the method of this invention is based on the concept of stopping the flow of blood through the damaged vessel. In forming a clot in a larger blood vessel, the blood is forced into surrounding vessels deeper below the surface of the skin. The larger, damaged vessel therefore shrinks in size as the blood it once contained is removed and becomes much less noticeable. In most applications, the needle 27 is inserted into the blood vessel 39 along all or at least a major portion of its length, and the laser source 17, preferably a relatively low energy source such as an argon laser, introduces a beam of less than 5 watts into the blood vessel 39.

A related procedure in which the laser optic device 11 of this invention may be utilized is the cosmetic elimination of relatively small blood vessels particularly on the face and/or legs of a patient. As is well known, laser energy and especially argon laser sources produce essentially white scar tissue in skin which is relatively smooth and cosmetically acceptable. In the method of this invention shown in FIG. 2, the needle 27 is inserted in the tissue 43 immediately adjacent an unsightly blood vessel 45 which is enlarged in the drawing for purposes of illustration. The laser source 17 is activated and laser energy of 2 to 5 watts, preferably from an argon laser source, is transmitted through the optic fiber 15 and needle 27 to the tissue 43 adjacent blood vessel 45. The heat generated by the laser energy causes the tissue 43 immediately surrounding and overlapping the blood vessel 45 to become scarred. This scarred tissue exerts pressure on the adjacent, relatively small blood vessels and effectively stops the flow of blood therethrough. As in the larger blood vessels described above, the blood flowing through such smaller vessels 45 finds a new path deeper below the skin which causes shrinkage of the treated vessel 45. Vessels 45 which have been shrunken are much less visible. In addition, the adjacent scarred tissue is white in appearance and tends to overlap and at least partially cover the treated vessel or vessels 45 to improve the cosmetic appearance of the affected area. This method of inserting the needle 27 in the tissue 43 adjacent the vessel 45, activating laser source 17 and removing needle 27 may be repeated at selected locations along the length of vessel 45, as in perivascular treatment, to create an area of substantially continuous scarred tissue 43 for completely covering the vessel 45.

In both of the methods for utilizing the laser optic device 11 herein, a small amount of blood may enter the needle 27. Laser energy from a source 17 such as an argon laser cannot penetrate the relatively opaque blood, and therefore creates clotting of the blood within the needle 27 which requires replacement, or at least cleaning, of the entire probe 23. To prevent clotting of blood within needle 27, the syringe 33 is operable to introduce saline or a similar rinsing solution into the needle 27 to flush the blood away. The saline is injected by syringe 33 into the catheter 13 and flows downwardly past the proximal end of optic fiber 15, without contacting its lens 16, into the hub 25 of probe 23 and then through the needle 27. The radial holder 22 contacts optic fiber 15 at two locations spaced about 180° apart, and presents no obstruction to the even flow of saline into needle 27. Once needle 27 is cleaned, the device 11 is ready for continued use.

It should be understood that the laser optic device of this invention may be utilized with diverse laser systems including, in addition to argon, laser sources such as ruby, carbon dioxide, chromium and a variety of others. In all of these systems, however, relatively low power levels (i.e. 3 to 5 watts) are required to perform the treatment methods of this invention, and thus no coolant systems are needed to cool the laser source or needle. Moreover, the diameter of the optic fiber utilized is widely variable depending on such factors as the size of the blood vessel to be treated. This invention provides an important advance over procedures involving the use of sclerosis solutions to induce clotting, and so-called electro-surgery. It has been found that chemical-induced clotting of the blood by solutions such as sclerosis solutions for purposes of cosmetic treatment of blood vessels or tissue creates reddening and potentially serious irritation of the skin. Electro-surgery involving the application of light or lasers to the skin's surface has proved to be equally damaging to the skin. By introducing a laser beam under the surface of the skin to a confined treatment area using the apparatus and methods of this invention, much improved cosmetic treatment of blood vessels has been achieved as compared to the prior art.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A laser optic device for the treatment of a blood vessel, comprising:
   a source of laser energy;
   a catheter communicating at one end with said source of laser energy;
   at least one optic fiber disposed within and protected by said catheter, said optic fiber being adapted to transmit said laser energy;
   a probe including a hub mounted to the other end of said catheter, and a hollow needle connected to said hub for receiving said laser energy, said needle being insertable within or adjacent to said blood vessel and being adapted to transmit said laser energy thereto;
   means for applying pressure to said blood vessel at a location spaced from the point of insertion of said needle in the direction of blood flow in said blood vessel; and
   rinsing means disposed along said catheter for rinsing said needle.

2. The laser optic device in claim 1 wherein said optic fiber includes a lens at its end adjacent said probe, said lens being adapted to focus said laser energy into and through said needle.

3. The laser optic device of claim 1 wherein said rinsing means is a syringe mounted to said catheter and containing rinsing solution, said syringe being operable to introduce said rinsing solution through said catheter and into said needle for rinsing blood therefrom.

4. A laser optic device for the treatment of a blood vessel, comprising:
   a source of laser energy;
   a catheter communicating at one end with said source of laser energy;
   at least one optic fiber disposed within and protected by said catheters, said optic fiber being adapted to transmit said laser energy;
   a probe mounted to the other end of said catheter and including a hollow needle for receiving said laser energy, said needle being insertable within or adjacent to said blood vessel and being adapted to transmit laser energy thereat; and
   rinsing means mounted to said catheter for rinsing said needle of blood from said blood vessel.

5. A method of creating a blood clot within a blood vessel comprising the steps of:
   inserting a probe within said blood vessel, said probe being operable to transmit laser energy produced by a laser energy source into said blood vessel;
   applying pressure to said blood vessel at a location spaced from the point of insertion of said probe in the direction of the flow of blood within said blood vessel; and
   activating said laser energy source, said laser energy being transmitted through said probe and entering the interior of said blood vessel causing a blood clot to form therewithin.

6. The method of claim 5 further including the steps of:
   removing said probe from the initial point of insertion into said blood vessel;
   reinserting said probe into said blood vessel at a point spaced from said initial point of insertion; and
   activating said laser energy source thereby creating further clotting of blood in said vessel to enlarge the size of said blood clot.

7. A method of cosmetically treating a damaged blood vessel comprising the steps of:
   initially inserting a probe within the body tissue at a first location immediately adjacent said blood vessel, said probe being adapted to transmit laser energy produced by a laser energy source to said first location;
   initially activating said laser energy source, said laser energy being transmitted through said probe and entering said tissue at said first location for scarring said tissue adjacent said blood vessel, said scarred tissue exerting pressure against said blood vessel to block the flow of blood therethrough and shrink said blood vessel, said scarred tissue at least partially visually obscuring said blood vessel adjacent said first location;

sequentially removing said probe from said tissue, inserting said probe into said tissue at a location spaced from said first location and then activating said laser energy source for the creation of scarred tissue adjacent said spaced location; and continuing said sequential operation of removing said probe, inserting said probe into said tissue and activating said laser energy source, said operation being continued at a plurality of selected locations in said tissue along the length of said blood vessel for the creation of substantially continuous scarred tissue along the entire length of said blood vessel.

* * * * *